United States Patent [19]

Kamegai et al.

[11] Patent Number: 5,015,414
[45] Date of Patent: May 14, 1991

[54] LOW-IRRITANT DETERGENT COMPOSITION CONTAINING ALKYL SACCHARIDE AND SULFOSUCCINATE SURFACTANTS

[75] Inventors: Jun Kamegai, Ichikawa; Hiromi Takamura; Hajime Hirota, both of Tokyo, all of Japan

[73] Assignee: Kao Corporation, Tokyo, Japan

[21] Appl. No.: 401,783

[22] Filed: Sep. 1, 1989

[30] Foreign Application Priority Data

Sep. 8, 1988 [JP] Japan ................. 63-225199

[51] Int. Cl.$^5$ .................. C11D 1/83; C11D 1/10; C11D 1/12; C11D 1/66
[52] U.S. Cl. ................. 252/545; 252/174.17; 252/546; 252/557; 252/DIG. 5; 252/DIG. 13
[58] Field of Search ............ 252/174.17, DIG. 5, 252/557, 546, 545, DIG. 13

[56] References Cited

U.S. PATENT DOCUMENTS

| | | | |
|---|---|---|---|
| 2,562,154 | 7/1961 | Vitalis | 252/541 |
| 2,562,155 | 7/1961 | Vitalis | 252/541 |
| 2,562,156 | 7/1961 | Vitalis | 252/541 |
| 2,562,159 | 9/1961 | Vitalis | 252/541 |
| 3,901,832 | 8/1975 | Dugan et al. | 252/557 |
| 4,604,282 | 8/1986 | Grollier et al. | 424/74 |
| 4,673,525 | 6/1987 | Small et al. | 252/132 |
| 4,749,515 | 6/1988 | Miyamoto et al. | 252/545 |
| 4,820,447 | 4/1989 | Medcalf, Jr. et al. | 252/117 |
| 4,839,098 | 6/1989 | Wisotzki et al. | 252/557 |

FOREIGN PATENT DOCUMENTS 0280143 8/1988 European Pat. Off. .
2166149 4/1986 United Kingdom .

OTHER PUBLICATIONS

Knaack, European Search Report, 07/17/90.

*Primary Examiner*—Paul Lieberman
*Assistant Examiner*—A. Beadles-Hay
*Attorney, Agent, or Firm*—Oblon, Spivak, McClelland, Maier & Neustadt

[57] ABSTRACT

A low-irritant detergent composition comprising alkyl saccharide surfactant and sulfosuccinate surfactant is disclosed. The detergent composition possesses excellent foaming capability and low-temperature stability. The detergent composition also imparts fine feeling when used as a detergent for the hair and the skin without irritation to the skin.

10 Claims, No Drawings

LOW-IRRITANT DETERGENT COMPOSITION CONTAINING ALKYL SACCHARIDE AND SULFOSUCCINATE SURFACTANTS

BACKGROUND OF THE INVENTION

1. Field of the Invention

The present invention relates to a low-irritant detergent composition, and, more particularly, to a detergent composition comprising an alkyl saccharide surfactant and a sulfosuccinate surfactant. The detergent composition possesses high foaming capability and low irritation to the skin. The detergent composition also imparts favorable feeling when used as a detergent for the hair or the skin without irritation.

2. Description of the Background Art

Nonionic surfactants have conventionally been used as a component for detergent compositions for the skin and the hair. They are less irritating in nature. However, since they are inferior in foaming capability to other types of surfactants, the amount which can be formulated is limited when they are incorporated especially in detergent compositions which call for high foaming properties, such as shampoos, body detergents, and the like. Some other drawbacks have accompanied the detergent compositions containing a single conventional nonionic surfactant, which include creaky feel upon use, poor foaming capability, and insufficient detergency when they are used as a detergent for the skin or the hair.

Among nonionic surfactants, alkyl saccharide surfactants have excellent foaming capability. Japanese Patent Application Laid-open No. 104625/1983 discloses compositions containing an alkyl saccharide surfactant together with an anionic surfactants such as alkylsulfate. The proposed compositions exhibit high foaming capability. They, however, provoke irritation to the skin or the scalp. Furthermore, compositions containing an alkyl saccharide surfactant having an alkyl group of $C_{10}$ or more are unstable at a low temperature and tend to precipitate.

There has existed, therefore, a desire to develop detergent compositions which are usable as a detergent for clothing, dish-washing, human body including the hair and the skin, and the like, and are stable and less irritating to the skin and the hair, and which can provide sufficient foaming capability and detergency.

In view of this situation, the present inventors have conducted extensive studies to solve the above problems, and, as a result, found that by formulating an alkyl saccharide surfactant together with a sulfosuccinate surfactant, the foaming capability could be improved and the composition was capable of producing creamy foam which gives excellent slippery feel to the skin when it was foamed. The inventors also found that the composition gave excellent feeling to the skin and the hair after washing without irritation to the skin and that the composition was also improved in low-temperature stability. These findings have led to the completion of this invention.

SUMMARY OF THE INVENTION

Accordingly, an object of the present invention is to provide a low-irritant detergent composition comprising an alkyl saccharide surfactant and a sulfosuccinate surfactant. In a preferred embodiment of the present invention, said alkyl saccharide surfactant is a compound represented by the following formula (I):

$$R_1-(OCH_2CH_2)_l-(G)_p \qquad (I)$$

wherein $R_1$ represents a $C_{8-18}$ linear or branched alkyl, alkenyl, or alkylphenyl group, G represents a $C_{5-6}$ reducing sugar, l denotes a number of 0 to 20, and p denotes a number of 1 to 10, and said sulfosuccinate surfactant is a compound represented by the following formula (II) or (III):

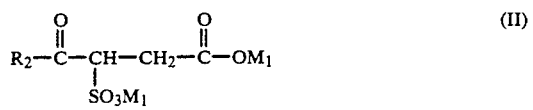

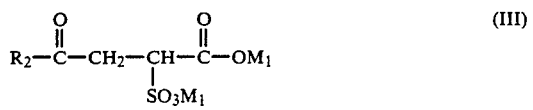

wherein $R_2$ represents $R_3-O-(CH_2CH_2O)_m-$ or $R_4CONH-(CH_2CH_2O)_m-$, wherein $R_3$ represents a $C_{8-22}$ linear or branched alkyl or alkenyl group, $R_4$ represents a $C_{7-21}$ linear or branched alkyl or alkenyl group, and m denotes a number of 0 to 20, and $M_1$ represents a hydrogen atom or a cation capable of forming a water-soluble salt and selected from the group consisting of an alkali metal, alkaline earth metal, ammonium and organic ammonium.

Other objects, features and advantages of the invention will hereinafter become more readily apparent from the following description.

DETAILED DESCRIPTION OF THE INVENTION AND PREFERRED EMBODIMENTS

There is no restriction to alkyl saccharide surfactants to be used in this invention inasmuch as they can be used for an ordinary detergent. Enumerated as examples of these alkyl saccharide surfactants are the compound represented by the following formula (I):

$$R_1-(OCH_2CH_2)_l-(G)_p \qquad (I)$$

wherein $R_1$ represents a $C_{8-18}$ linear or branched alkyl, alkenyl, or alkylphenyl group, G represents a $C_{5-6}$ reducing sugar, l denotes a number of 0 to 20, and p denotes a number of 1 to 10.

$R_1$ in formula (I) is a $C_{8-18}$ linear or branched alkyl, alkenyl, or alkylphenyl group. Given as preferable examples of $R_1$ are $C_{9-14}$ linear or branched alkyl groups such as a nonyl group, a decyl group, a lauryl group, myristyl group, and the like. The basic unit of a hydrophilic saccharide portion is a $C_{5-6}$ reducing sugar (G in formula (I)). Given as preferable examples of the reducing sugar are glucose, galactose, and fructose. The degree of polymerization (S) of saccharide (p in formula (I)) is in the range of 1 to 10 as mentioned above. When the property of the compounds of formula (I) due to the group $R_1$ is taken into account, the value for the polymerization (S) of 1 to 1.4 is desirable for the $R_1$ group with $C_{8-11}$, and (S) of 1.5 to 4.0 is desirable for the $R_1$ group with $C_{12-14}$. From the aspect of securing good foaming capability, it is preferable that the polymerization degree (S) of saccharide be in the range of 1 to 1.4 in a mixed surfactant composition of an alkylsaccharide surfactant and a sulfosuccinate surfactant. The foaming capability decreases with an increase in the polymerization degree. The mean value of polymerization degree (S) can be determined by the Proton-NMR method.

Given as examples of the alkyl saccharide surfactant are β-alkyl saccharides synthesized by known Koenings-Knorr method, such as octyl glucoside, nonyl glucoside, decyl glucoside, decyl maltoside, tridecyl maltoside, polyoxyethylene(EO=2)dodecylglucoside and the like [alkyl saccharides produced from a higher alcohol, polyoxyethylene alkylether alcohol, and a reducing sugar such as glucose, galactose, maltose, and the like (U.S. Pat. No. 3,839,318 and U.S. Pat. No. 3,598,865)].

The alkyl saccharide surfactant of this invention is incorporated in an amount of 1 to 60% by weight. It is desirable that the surfactant be formulated into the detergent composition of this invention in an amount of 2 to 30% by weight if the composition is a shampoo, 5 to 50% by weight if the composition is a detergent for the skin, and 2 to 40% by weight if the composition is a dish-washing detergent.

There is no restriction to a sulfosuccinate surfactant of the present invention insofar as it can be used for an ordinary detergent composition Given as examples of a sulfosuccinate surfactant are sulfosuccinates of higher alcohols or their ethoxylates; or sulfosuccinates derived from higher fatty acid amides represented by formula (II) or (III):

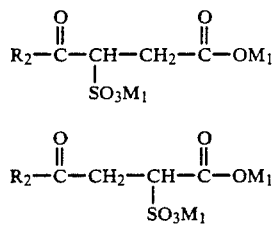

wherein $R_2$ represents $R_3-O-(CH_2CH_2O)_m-$ or $R_4CONH-(CH_2CH_2O)_m-$ (wherein $R_3$ represents a $C_{8-22}$ linear or branched alkyl or alkenyl group, $R_4$ represents a $C_{7-21}$ linear or branched alkyl or alkenyl group, and m denotes a number of 0 to 20), and $M_1$ represents a hydrogen atom or a cation capable of forming a water-soluble salt and selected from the group consisting of an alkali metal, alkaline earth metal, ammonium and organic ammonium.

Given as examples of a sulfosuccinate of higher alcohol or its ethoxylate, the compounds represented by formula (II) or (III), are a disodium salt of sulfosuccinate of a secondary alcohol having 11 to 13 carbons [Softanol MES 3, 5, 7, 9, 12, manufactured by NIPPON SHOKUBAI KAGAKU KOGYO CO., LTD (each number denotes an average addition mol of ethylene oxide (EO))], a di-sodium salt of sulfosuccinate of lauryl alcohol or lauryl alcohol ethoxylate (EO=3, 4, 6, 9, 12, Kohacool L-400, etc., manufactured by Toho Chemical Industries Co., Ltd.), a di-sodium salt of sulfosuccinate of synthetic primary alcohol with a $C_{12-15}$ carbon content or its ethoxylate (EO=2-12), a di-sodium salt of sulfosuccinate of Guerbet alcohol with a $C_{8-12}$ carbon content or its ethoxylate (EO=2-12), and the like. Given as examples of the sulfosuccinate derived from a higher fatty acid amide are a di-sodium salt of sulfosuccinate of polyethylene glycol (EO=1, 2) amide laurate, a di-sodium salt of sulfosuccinate of polyethylene glycol (EO=1, 2) oleate, a di-sodium salt of sulfosuccinate of coconut oil fatty acid polyethylene glycol (EO=4), and the like. Among these, a linear mono higher alcohol succinate with a $C_{11-13}$ carbon content is preferable in view of agreeable feel and foaming capability. It is desirable that a sulfosuccinate surfactant be incorporated in an amount of 1 to 60% by weight into the detergent composition of this invention, with particularly desirable amount being 2 to 20% by weight when it is used as a surfactant of a shampoo, 5 to 50% by weight when it is used as a surfactant of a detergent for the skin, and 2 to 40% by weight when it is used as a surfactant of a dish-washing detergent.

It is preferable that the total amount of an alkyl saccharide surfactant and a sulfosuccinate surfactant to be incorporated into the detergent composition of the present invention be 5–90% by weight with 10 to 60% by weight being particularly preferable. The proportion of an alkyl saccharide surfactant/a sulfosuccinate type surfactant may be arbitrarily selected in the range of 1:9 to 9:1. The range of 1:4 to 4:1 is particularly preferable.

The detergent composition of this invention is preferably adjusted to pH 3 to 10 by adding known acidic or alkaline agents. It is particularly preferable that the pH of the detergent composition be adjusted to 4 to 8.

In addition to the above essential ingredients, conventional components used for detergents may be arbitrarily incorporated into the composition of this invention to the extent that the effect of the invention is not impaired. Given as examples of these components are humectants such as propylene glycol, glycerol, sorbitol, and the like; viscosity modifiers such as methyl cellulose, carboxylvinyl polymer, hydroxyethyl cellulose, polyoxyethyleneglycol distearate, ethanol, and the like; pearling agents; perfumes; coloring agents; UV ray absorbers; anti-oxidants; germicides such as trichlosan, trichlorocarban, and the like; antiphlogistics such as potassium glycyrrhizate, tocopherol acetate, and the like; antimicrobial agents such as methylparabene, butylparabene, and the like; solubilizing agents such as sodium or potassium salt of toluenesulfonic acid or xylenesulfonic acid, urea, and the like; viscosity adjusting agents such as a mineral clay, a water-soluble polymer, and the like; water-insoluble abradants such as calcite, fluorite, calcium phosphate, zeolite, polyethylene, nylon, polystyrene, and the like; enzyme, and the like.

The detergent compositions of the present invention can be used as various detergents such as detergents for clothing, dish-washing detergents, detergents for the hair and the skin, and the like. The detergent composition of this invention may be formed into any forms known to the art to be adopted for detergents. It is desirable that the total content of an alkyl saccharide surfactant and a sulfosuccinate surfactant to be incorporated into the detergent composition be above 30% by weight if the formulation is a solid type, above 20% by weight if the formulation is a paste type, and above 10% by weight if the formulation is a liquid type.

Other features of the invention will become apparent in the course of the following description of the exemplary embodiments which are given for illustration of the invention and are not intended to be limiting thereof.

EXAMPLES

EXAMPLE 1

The detergent compositions (pH 7) having the formulation shown in Table 1 below were prepared. Foam amount, foam quality, feeling to the hair and the skin, storage stability, irritation to the skin of the compositions were evaluated.

Foam quality, feeling to the hair and the skin, and irritation to the skin were evaluated by the following method. 1 gm of the detergent composition was applied onto healthy Japanese woman's hair weighing 10 gm and 15 cm wide. The hair immediately after the detergent was foamed for one minute and the hair which was rinsed and then dried with a drier were respectively subjected to evaluation. While, 1 gm of the detergent was taken on the palm of the hand and foamed by adding an appropriate amount of water. The skin of the hand immediately after foam was made and the skin after rinsed and dried were evaluated. The evaluation was conducted by a panel consisting of 5 specialists. The foam amount was determined by reverse stirring method.

The low-temperature stability of the detergent compositions were evaluated by observing by naked eyes after they were stored at 5° C. and −5° C. for one month.

The irritation to the skin of the detergent composition was evaluated on the skin of a guinea pig after the skin was washed seven times with 25% aqueous solution of the detergent.

Evaluation Standard

Foam amount

AAA: abundant foam was observed
BBB: insufficient foam was observed
CCC: little foam was observed

Foam quality

AAA: creamy and slippery
BBB: a bit coarse and not a bit slippery
CCC: coarse and non slippery

Feel to the hair and the skin

AAA: not creaky and agreeable
BBB: rather strongly creaky and slightly objectionable
CCC: strongly creaky and objectionable

Low-temperature stability

AAA: transparent
BBB: slightly turbid
CCC: turbidity or precipitate occurred

Irritation to the skin

AAA: non irritant or slightly irritant
BBB: weakly irritant
CCC: moderately and acutely irritant

TABLE 1

| Component | Inventive composition |  |  |  |  |  |  |  |  |
|---|---|---|---|---|---|---|---|---|---|
|  | 1 Wt % | 2 Wt % | 3 Wt % | 4 Wt % | 5 Wt % | 6 Wt % | 7 Wt % | 8 Wt % | 9 Wt % |
| AS-TEA *1 | — | — | — | — | — | — | — | — | — |
| Disodium polyoxyethylene(4) monolauryl sulfosuccinate | 10.0 | — | — | 10.0 | 10.0 | — | — | — | — |
| Disodium monolauryl sulfosuccinate | — | 10.0 | — | — | — | 10.0 | 10.0 | — | — |
| Disodium polyoxyethylene(5) lauroylethanolamide sulfosuccinate | — | — | 10.0 | — | — | — | — | 10.0 | 10.0 |
| Decylpolyglycoside (p = 1.4) *2 | 5 | — | — | — | — | 5 | — | 5 | — |
| Decylpolyglycoside (p = 1.3) *2 | — | — | — | 5 | — | — | — | — | 10.0 |
| α-Dodecylpolyglycoside (p = 1.8) *2 | — | 5 | — | — | — | — | — | — | 5 |
| Dodecylpolyglycoside (p = 2.5) *2 | — | — | 5 | — | 5 | — | 5 | — | — |
| Tap Water | Balance | Balance | Balance | Balance | Balance | Balance | Balance | Balance | Balance |
| Foam amount | AAA | BBB | BBB | AAA | BBB | AAA | AAA | AAA | AAA |
| Foam quality | AAA | AAA | AAA | AAA | AAA | AAA | AAA | AAA | AAA |
| Feeling to the hair | AAA | AAA | AAA | AAA | AAA | AAA | AAA | AAA | AAA |
| Feeling to the skin | AAA | AAA | AAA | AAA | AAA | AAA | AAA | AAA | AAA |
| Low temperature stability | AAA | AAA | AAA | BBB | BBB | AAA | AAA | AAA | AAA |
| Irritation to the skin | AAA | AAA | AAA | AAA | AAA | AAA | AAA | AAA | AAA |

| Component | Comparative composition |  |  |  |  |  |  |
|---|---|---|---|---|---|---|---|
|  | 1 Wt % | 2 Wt % | 3 Wt % | 4 Wt % | 5 Wt % | 6 Wt % | 7 Wt % |
| AS-TEA *1 | — | — | — | — | — | 15 | 15 |
| Disodium polyoxyethylene(4) monolauryl sulfosuccinate | — | — | — | — | 15 | — | — |
| Disodium monolauryl sulfosuccinate | — | — | — | — | — | — | — |
| Disodium polyoxyethylene(5) lauroylethanolamide sulfosuccinate | — | — | — | — | — | — | — |
| Decylpolyglycoside (p = 1.4) *2 | 15 | — | — | — | — | — | — |
| Decylpolyglycoside (p = 1.3) *2 | — | 15 | — | — | — | — | — |
| Dodecylpolyglycoside (p = 1.8) *2 | — | — | 15 | — | — | — | — |
| Dodecylpolyglycoside (p = 2.5) *2 | — | — | — | 15 | — | — | — |
| Tap Water | Balance | Balance | Balance | Balance | Balance | Balance | Balance |
| Foam amount | BBB | BBB | BBB | BBB | AAA | AAA | AAA |
| Foam quality | BBB | BBB | BBB | BBB | AAA | AAA | AAA |
| Feeling to the hair | BBB | BBB | BBB | BBB | BBB | BBB | AAA |
| Feeling to the skin | BBB | BBB | BBB | BBB | BBB | CCC | BBB |
| Low temperature stability | CCC | CCC | CCC | CCC | CCC | AAA | CCC |

TABLE 1-continued

| Irritation to the skin | AAA | AAA | AAA | AAA | BBB | CCC | CCC |
| --- | --- | --- | --- | --- | --- | --- | --- |

Note: Unit of the value in Table is % by weight
*1 Emal TDD (manufactured by Kao Corporation)
*2 p denotes a number of saccharide polymerization.

EXAMPLE 2

Shampoo

| | |
| --- | --- |
| (1) $C_{10}$-$(G)_{1.45}$ *1 | 8 wt % |
| (2) Disodium polyoxyethylene(2) laurylsuccinate | 12 wt % |
| (3) Coconut oil fatty acid diethanol amide | 5 wt % |
| (4) Cationized cellulose *2 | 0.3 wt % |
| (5) Perfume | slight amount |
| (6) Coloring substance | slight amount |
| (7) Salt | 1 wt % |
| (8) Purified water | Balance |

*1 $C_{10}$: Decyl group G: Glucose residual group
*2 Polymer JR400 (manufactured by Union Carbide Co.)

Preparation Components (1), (2), (3), and (6) were dissolved in purified water which was heated to 60° C. After the dissolution was confirmed, the mixed solution was cooled and components (4) and (5) were added to the solution. The shampoo composition obtained did not give frictional feeling to the hair and easily rinsed. The shampoo also exhibited fine feeling upon use and excellent foaming capability as well as excellent low-temperature stability.

EXAMPLE 3

Cleansing foam

| | |
| --- | --- |
| (1) $C_{12}$-$(EO)_2$-$(G)_{2.5}$ *3 | 30 wt % |
| (2) Disodium laurylsulfosuccinate | 30 wt % |
| (3) Lauric acid | 4 wt % |
| (4) Ethyleneglycol distearate *4 | 4 wt % |
| (5) Perfume | slight amount |
| (6) Purified water | Balance |

*3 $C_{12}$: Lauryl group G: Glucose residual group
*4 Emanone 3201M (manufactured by Kao Corporation)

Preparation

Components (1), (2), (3), and (4) were dissolved in purified water which was heated to 70° C. After the dissolution was confirmed, the mixed solution was cooled to 40° C. Component (5) was added to the solution and the mixture was cooled. The cleansing foam obtained exhibited abundant lather and it was readily rinsed. The cleansing foam also imparted slippery and moisturized feeling to the skin after it was dried.

EXAMPLE 4

Dish-washing detergent

| | |
| --- | --- |
| (1) $C_{10.2}$-$(G)_{1.3}$ *1 | 15 wt % |
| (2) Disodium Polyoxyethylene(3) laurylsuccinate | 5 wt % |
| (3) Lauryl dimethylamineoxide | 2 wt % |
| (4) Ethanol | 3 wt % |
| (5) Perfume | Slight amount |
| (6) Coloring substance | Slight amount |
| (7) Tap water | Balance |

*1 $C_{10.2}$: Average carbon numbers of the mixture of $C_9$, $C_{10}$, $C_{11}$ G: Glucose residual group

Preparation

Components (1), (2), (3), (4), and (6) were added to water to dissolve. Component (5) was then added to the solution.

The dish-washing detergent obtained had high detergency and excellent foaming capability. The detergent also imparted fine feeling upon use and good rinsing capability.

EXPERIMENTAL EXAMPLE 1

The effect of polymerization degree (S) of saccharide (p in formula (I)) on foaming capability of a detergent was investigated. The tests were performed using 0.3% of decyl polyglycosides having polymerization degrees (S) shown in Table 2 and 0.2% of disodium polyoxyethylene(EO=3)monolauryl sulfosuccinate according to a reverse stirring method using 0.5% lanolin. The results are shown in Table 2.

TABLE 2

| Polymerization degree | Foam amount (ml) |
| --- | --- |
| p = 1.15 | 223 |
| p = 1.4 | 206 |
| p = 1.8 | 180 |
| p = 1.15 | 130 |

Obviously, numerous modifications and variations of the present invention are possible in light of the above teachings. It is therefore to be understood that within the scope of the appended claims, the invention may be practiced otherwise than as specifically described herein.

What is claimed is:

1. A low-irritant detergent composition comprising an alkyl saccharide surfactant and a sulfosuccinate surfactant in weight proportion of 1:9 to 9:1, wherein said alkyl saccharide surfactant is a compound represented by the following formula (I):

$$R_1-(OCH_2CH_2)l-(G)p \qquad (I)$$

wherein $R_1$ represents a $C_8$–$C_{18}$ linear or branched alkyl, alkenyl, or alkylphenyl group, G represents a $C_5$–$C_6$ reducing sugar, l denotes a number of 0 to 20, and p denotes a number of 1 to 10, and wherein said sulfosuccinate surfactant is a compound represented by the following formula (II) or (III):

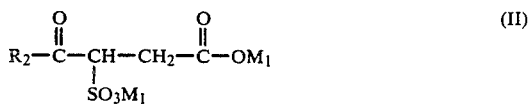

$$R_2-\overset{O}{\underset{}{C}}-\underset{SO_3M_1}{\overset{}{CH}}-CH_2-\overset{O}{\underset{}{C}}-OM_1 \qquad (II)$$

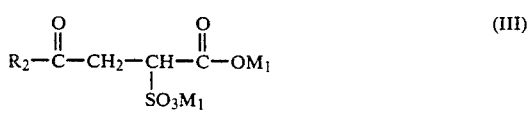

$$R_2-\overset{O}{\underset{}{C}}-CH_2-\underset{SO_3M_1}{\overset{}{CH}}-\overset{O}{\underset{}{C}}-OM_1 \qquad (III)$$

wherein $R_2$ represents $R_3-O-(CH_2CH_2O)_m-$ or $R_4CONH-(CH_2CH_2O)_m-$, wherein $R_3$ represents a $C_8$–$C_{22}$ linear or branched alkyl or alkenyl group, $R_4$ represents a $C_7$–$C_{21}$ linear or branched alkyl or alkenyl group, and m denotes a number of 0 to 20, and $M_1$ represents a hydrogen atom or a cation capable of forming a water-soluble salt and selected from the group consisting of an alkali metal, alkaline earth metal, ammonium and organic ammonium.

2. The low-irritant detergent composition according to claim 1, wherein the weight proportion of alkyl saccharide to sulfosuccinate is 1:4 to 4:1.

3. The low-irritant detergent composition according to claim 1, wherein each of the alkyl saccharide and sulfosuccinate is present in an amount of 1–60% by weight.

4. The low-irritant detergent composition according to claim 2, wherein each of the alkyl saccharide and sulfosuccinate is present in an amount of 1–60% by weight.

5. A low-irritant detergent shampoo composition according to claim 1 wherein the alkyl saccharide is present in an amount of 2–30% by weight and the sulfosuccinate is present in an amount of 2–20% by weight.

6. A low-irritant detergent shampoo composition according to claim 2 wherein the alkyl saccharide is present in an amount of 2–30% by weight and the sulfosuccinate is present in an amount of 2–20% by weight.

7. A low-irritant detergent skin composition according to claim 1 wherein the alkyl saccharide and sulfosuccinate each are present in an amount of 5–50% by weight.

8. A low-irritant detergent skin composition according to claim 2 wherein the alkyl saccharide and sulfosuccinate each are present in an amount of 5–50% by weight.

9. A low-irritant detergent dishwashing composition according to claim 1 wherein each of the alkyl saccharide and sulfosuccinate is present in an amount of 2–40% by weight.

10. A low-irritant detergent dishwashing composition according to claim 2 wherein each of the alkyl saccharide and sulfosuccinate is present in an amount of 2–40% by weight.

* * * * *